US012152280B2

(12) United States Patent
Zevallos et al.

(10) Patent No.: US 12,152,280 B2
(45) Date of Patent: Nov. 26, 2024

(54) DRAIN FLUID FOR DIAGNOSTICS

(71) Applicants: DROPLET BIOSCIENCES INC., Cambridge, MA (US); The Washington University, St. Louis, MO (US)

(72) Inventors: Jose P. Zevallos, St. Louis, MO (US); Aadel Chaudhuri, Chesterfield, MO (US); Stanley N. Lapidus, Golden, CO (US)

(73) Assignees: DROPLET BIOSCIENCES, INC., Cambridge, MA (US); The Washington University, St. Louis, MO (US)

( * ) Notice: Subject to any disclaimer, the term of this patent is extended or adjusted under 35 U.S.C. 154(b) by 0 days.

(21) Appl. No.: 17/491,237

(22) Filed: Sep. 30, 2021

(65) Prior Publication Data

US 2023/0092038 A1 Mar. 23, 2023

Related U.S. Application Data

(60) Provisional application No. 63/246,253, filed on Sep. 20, 2021.

(51) Int. Cl.
*C12Q 1/6886* (2018.01)
*C12Q 1/6883* (2018.01)

(52) U.S. Cl.
CPC ......... *C12Q 1/6886* (2013.01); *C12Q 1/6883* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 4,957,484 A | 9/1990 | Murtfeldt | |
| 6,022,333 A | 2/2000 | Kensey | |
| 6,187,536 B1 | 2/2001 | Weinberg et al. | |
| 6,190,347 B1 | 2/2001 | Kensey | |
| 7,267,671 B2 | 9/2007 | Shehada | |
| 7,727,720 B2 | 6/2010 | Dhallan | |
| 7,918,822 B2 | 4/2011 | Kumar et al. | |
| 9,187,786 B2 | 11/2015 | Hoque et al. | |
| 9,421,316 B2 | 8/2016 | Leeflang et al. | |
| 9,678,075 B2 | 6/2017 | Schroder et al. | |
| 9,682,223 B2 | 6/2017 | Callaghan et al. | |
| 10,052,059 B2 | 8/2018 | Callaghan et al. | |
| 10,338,073 B2 | 7/2019 | Osarogiagbon | |
| 10,726,943 B2 | 7/2020 | Stojadinovic et al. | |
| 10,865,452 B2 | 12/2020 | Davicioni | |
| 2003/0215805 A1 | 11/2003 | Lillie et al. | |
| 2007/0141582 A1 | 6/2007 | Li et al. | |
| 2010/0190662 A1 | 7/2010 | Sutphen et al. | |
| 2011/0159509 A1 | 6/2011 | Hoon et al. | |
| 2011/0287412 A1* | 11/2011 | Landthaler | C12N 15/1058 435/6.1 |
| 2013/0137593 A1 | 5/2013 | Nissan et al. | |
| 2014/0005058 A1* | 1/2014 | Watson | C12Q 1/6809 506/7 |
| 2015/0140041 A1* | 5/2015 | Vitiello | A61K 39/0011 424/277.1 |
| 2015/0315289 A1 | 11/2015 | Liu et al. | |
| 2016/0033511 A1 | 2/2016 | Pannell et al. | |
| 2016/0363596 A1 | 12/2016 | Depinho et al. | |
| 2017/0211153 A1 | 7/2017 | Kohli et al. | |
| 2017/0276674 A1 | 9/2017 | Hamm-Alvarez | |
| 2018/0252722 A1 | 9/2018 | Wang | |
| 2019/0060546 A1 | 2/2019 | Callaghan et al. | |
| 2019/0219584 A1 | 7/2019 | Hoffmann et al. | |
| 2019/0256924 A1* | 8/2019 | Vogelstein | C12Q 1/686 |
| 2020/0109456 A1 | 4/2020 | Meissner et al. | |
| 2020/0157636 A1 | 5/2020 | Velculescu et al. | |
| 2020/0258601 A1* | 8/2020 | Lau | G16H 50/20 |
| 2020/0263167 A1 | 8/2020 | Van Den Boom et al. | |
| 2020/0300747 A1 | 9/2020 | Kim et al. | |
| 2020/0377960 A1 | 12/2020 | Shah | |

FOREIGN PATENT DOCUMENTS

| | | |
|---|---|---|
| WO | 2017/217700 A1 | 12/2017 |
| WO | 2019/133391 A1 | 7/2019 |
| WO | 2019130117 A1 | 7/2019 |
| WO | 2020169799 A1 | 8/2020 |
| WO | 2020169819 A1 | 8/2020 |
| WO | 2021/127065 A1 | 6/2021 |

OTHER PUBLICATIONS

Escudero et al. Nature Communications. 2020. 11:5376, p. 1-11 (Year: 2020).*
Garcia-Silva et al. JEM. 2019. 216(5): 1061-1070 and Supplemental material S1-S10 (Year: 2019).*
Pentsova et al J Clin Oncology. 2016. 34(20): 2404-2415 (Year: 2016).*
Nathanson et al Biochem Pharmacol. 2010. 805: 755-761 (Year: 2010).*
Broggi et al J. Exp. Med. Apr. 2019. 216(5): 1091-1107 and Supplemental material, 23 pages total (Year: 2019).*
Norman et al (Intracavity lavage and wound irrigation for prevention of surgical site infection (Review). Cochrane Database of Systematic Reviews, John Wiley & Sons publisher. (Year: 2017).*
Nowecki et al. British J Dermatology. 2008. 159: 597-605 (Year: 2008).*
Chun, 2017, Medical suction and fluid waste management, a White Paper by Joint Commission International (16 pages).
Dudley, 2021, Detection and diagnostic utilization of cellular and cell-free tumor DNA, Ann Rev Pathol Mech Dis 16:199-22.
Han, 2020, Lymph liquid biopsy for detection of cancer stem cells, Cytometry A 99(5):496-502.

(Continued)

*Primary Examiner* — Carla J Myers

(74) *Attorney, Agent, or Firm* — Withers Bergman LLP; Thomas C. Meyers

(57) ABSTRACT

The present invention provides methods for testing surgical fluid for biomarkers of disease, including cancer.

14 Claims, No Drawings

(56) References Cited

OTHER PUBLICATIONS

Lassig, 2017, Association of oral cavity and oropharyngeal cancer biomarkers in surgical drain fluid with patient outcomes, JAMA Otolaryl Head Neck Surg 143(7):670-678.

Masago, 2018, Targeting minimial residual disease after surgery with molecular targeted therapy, J Thorac Dis 10 (Suppl 17):s1982-s1985.

Mohammed, 2019, Lymph-circulating tumor cells show distinct properties to blood-circulating tumor cells and are efficient metastatic precursors, Mol Oncol 13:1400-1418.

Serres, 2019, Optimizing surgical fluid management practices based on collection and disposal volumes, White Paper (8 pages).

Tsujinaka, 2011, Drain vs no drain after colorectal surgery, Ind J Surg Oncol 2(1):3-8.

International Search Report and Written Opinion for International Application No. PCT/US2022/031979, mailed Sep. 2, 2022, 11 Pages.

International Search Report and Written Opinion for International Application No. PCT/US2020/065446, mailed Apr. 14, 2021, 11 Pages.

* cited by examiner

DRAIN FLUID FOR DIAGNOSTICS

FIELD OF INVENTION

The invention related to diagnostic methods for identifying biomarkers indicative of disease.

BACKGROUND

Cancer is a leading cause of death globally. Early detection, while beneficial for most cancers, is often difficult. In part, this is because many cancers first develop without presenting any specific clinical symptoms, and diagnosis only occurs when the disease has reached a stage when it is difficult to treat.

Cancer detection has focused on liquid biopsy in blood or plasma for the detection of cell-free tumor DNA. Blood is of high clinical interest because of its accessibility. Unfortunately, many of these methods lack sensitivity. As a result, early cancer detection, when tumor DNA is present as only a minute fraction of the DNA collected from blood or plasma, is often difficult. Moreover, due to the lack of sensitivity, progression of the disease and its response to therapeutic intervention are difficult to monitor.

Tissue, such as tumor tissue, generally is the most informative sample for diagnosis and prognosis of cancer. Unfortunately, tissue samples are often difficult to access and subject to limited availability, especially without performing an invasive procedure. In the context of cancer, often by the time tumors are detected, cancer has spread or progressed.

Consequently, physicians and patients are often unable to make timely, informed decisions regarding therapeutic intervention.

SUMMARY

The present invention provides methods for using drain fluid (i.e., effluent) obtained from medical procedures (e.g., medical interventions such as surgeries, biopsies, catheterizations, dissections, intubations and the like) to assess diagnostic biomarkers indicative of disease. According to the invention and contrary to conventional thinking, waste fluid is actually a rich source of diagnostic information. According to the invention, drain fluid is used as a source of biomarkers indicative of disease. The drain fluid can be obtained as effluent from a medical intervention, such as a surgery or biopsy. Drain fluid can also be obtained during treatment of a wound or interventional procedure. Methods taught herein provide sensitive and specific diagnostics that allow assessment of disease status, staging, and progression; as well as aiding in therapeutic selection and assessment of therapeutic efficacy.

The present invention is useful for evaluation of any disease biomarker. In a preferred embodiment, drain fluid is a source of circulating tumor DNA (ctDNA), tumor cells, ratios of ctDNA to cells, mutations associated with cancer, oncogenes and the like. The invention is also useful for the assessment of diseases other than cancer, including infectious diseases, autoimmune diseases, endocrine diseases and the like.

Drain fluid may comprise a combination of irrigation fluid, blood, plasma, cells, and lymphatic fluid. Accordingly, it may be necessary to isolate a fraction of interest from the drain fluid. However, the invention contemplates that raw drain fluid contains a sufficient amount of diagnostic content that it can be used without any significant sample preparation.

Accordingly, the present invention provides methods for disease diagnosis comprising the steps of obtaining drain fluid from a medical intervention, identifying in the fluid a biomarker indicative of disease, and diagnosing a disease or condition based on the presence of the biomarker in the fluid. The disease can be any disease, including cancer, infectious disease, metabolic disease or an autoimmune disease. However, the invention has particular application in the diagnosis of cancer.

Drain fluid for use in the invention preferably is surgical drain fluid, for example surgical fluid that would otherwise be discarded as medical waste. Surgical drain fluid may comprise blood, plasma, aggregated tissue, irrigation fluid, lymphatic fluid, lymphovascular fluid, interstitial fluid or a combination thereof. The fluid may further comprise bile, sweat, semen, vaginal secretions, cerebrospinal fluid, synovial fluid, pleural fluid, peritoneal fluid, pericardial fluid, amniotic fluid, saliva, or mucus depending on the location from which it is obtained.

Identification of a biomarker indicative of disease in the drain fluid may be accomplished by any known method for biomarker detection. For example, biomarkers for disease may be detected by sequencing, for example protein or nucleic acid sequencing. The biomarker may be DNA and/or RNA. Accordingly, methods of the present invention contemplate creating a genomic profile from DNA or RNA in the drain fluid. The profile may be a patient's germ line profile or may be of a tumor.

Biomarkers for use in the invention may be any known biomarker for disease. For example, the biomarker may be a nucleic acid (DNA, any RNA species), a protein, any other molecule or compound, or a cell. The origin of the biomarker may be an organism, for example a bacterium, a fungus, an animal cell, a tumor cell, a protozoan cell, or a virus. The choice of specific biomarkers is dependent on their sensitivity and specificity of the biomarker for a particular condition, and also on technical aspects related to collection protocols, stability and detection from biological samples. In certain embodiments, the biomarker may be one or more of interleukin-1, interleukin-6, interleukin-10, a tumor necrosis factor, matrix metalloproteinase-1, matrix metalloproteinase-2, matrix metalloproteinase-9, matrix metalloproteinase-13, or a nucleic acid comprising a mutation.

Biomarkers are correlated with the diagnosis, prognosis, staging and development of disease; as well as therapeutic selection and response. In clinical oncology, early diagnosis and prognosis is critical for appropriate therapeutic intervention. For example, treatment protocols may be different if there are indications of metastatic disease in cancer. Accordingly, biomarkers detected in drain fluid may depend on the purpose for the assessment, e.g., to indicate normal biological processes, pathogenic processes, or pharmacologic response to therapeutic intervention.

The present invention also contemplates the discovery that lymphatic fluid in surgical effluent frequently contains important biomarkers, often in greater abundance than in blood and plasma. Accordingly, methods of the invention may comprise the further step of separating lymphatic fluid from the overall drain fluid. Methods of the invention may also comprise assaying the surgical fluid without separating lymphatic fluid from the drain fluid.

The invention contemplates the detection of a ratio of circulating tumor cells to cell-free DNA. In addition, the invention contemplates detecting an amount of a biomarker in drain fluid as compared to blood, plasma, or lymph node tissue from the same subject at the same time or at intervals over a period of time. As discussed above, it has been discovered by the present invention that surgical drain fluid may comprise a greater ratio of circulating tumor cells to cell-free DNA than the same volume of blood or plasma. Without being bound to a single theory, this may be the result of large quantities of biomarker rich lymphatic fluid in the surgical waste. Accordingly, if the subject is afflicted with a disease condition, the lymphatic fluid separated from, for example, a surgical effluent may comprise a greater volume of cells or nucleic acid molecules specific to a tumor than the same volume of blood obtained from the subject.

Drain fluid may be obtained by any known method. For example, the drain fluid may be obtained using a catheter or a drain port and may be actively or passively collected. Suction drainage, for example using a vacuum, may also be used to obtain fluids during a surgical procedure. The surgical drain fluid may be collected by using a syringe, pipet, or catheter, for example a Jackson-Pratt (JP) drain. The drain fluid may be collected in or transferred to a container, for example a sample vessel, such as a vial, flask, or ampule, suitable for the sterile collection of medical specimens. Surgical fluid may also be collected from biohazard waste containers, for example a suction canister, filled during a procedure or diverted from a biohazard waste container during a surgical procedure. Sample may be obtained by irrigating a surgical wound. Irrigating fluid may comprise water, saline, antibiotic solutions, antiseptic agents, or a combination thereof.

Surgical drain fluid may be collected from any surgical procedure. For example, the surgery may comprise an open surgical procedure or an endoscopic procedure. The surgical procedure may comprise an invasive procedure. The surgical procedure may comprise a resection, biopsy, dissection, or excision. The surgical procedure may be a thoracentesis. The surgical procedure may be a minimally invasive procedure, such as, for example, a stent placement.

The surgical procedure may be a procedure that is not a related to a disease being diagnosed. Thus, the invention applies to any disease condition and the drain fluid may be from an unrelated interventional procedure.

Drain fluid may be obtained at any time during or following an interventional procedure. For example, drain fluid may be collected at the time of intervention and then periodically over the course of hours, days or weeks.

The present invention also contemplates diagnosing disease by obtaining a representative sample of drain fluid and assaying the drain fluid for indicia of disease. Obtaining a representative sample is especially important in cancer diagnosis because tumor-related biomarkers may not be present uniformly in the drain fluid, depending on volume, source of the drain fluid and collection techniques.

The drain fluid may be collected via a drain. For example, the drain may be designed to be maintained at a wound site for a period of time after a surgical procedure.

Methods of the invention are useful for assessing disease severity. For example, cancer metastasis may be identified by identifying a cancer biomarker in drain fluid and determining whether the same biomarker is present in a lymph node or in blood. If the biomarker is found in the drain fluid but not in blood, it can be inferred that the tumor cells have yet reached the general circulation.

Similarly, the presence of disease-associated biomarkers in drain fluid, lymphatic channels, lymph glands and blood is useful to determine systemic spread. For example, a DNA sample from a tumor may be obtained as well as a blood sample and surgical fluid. Each of the samples may be then tested for tumor DNA, and the ratios of tumor DNA in the tumor, lymphatic fluid, and blood may be used as an indicator of disease staging.

Methods of the invention also contemplate assessment of pharmaceutical efficacy. According to the invention, accumulation of tumor DNA in drain fluid after therapy is indicative that the therapy is effective, as an increase in tumor DNA in drain fluid after therapy is indicative of the induction of cell death in the tumor. Thus, real-time measurement during therapy is indicative of therapeutic efficacy. Thus, the efficacy of systemic therapy is measure by the concentration of local biomarkers in the drain fluid. These methods are agnostic in terms of biomarker content.

According to methods of the invention the rate of accumulation or decrease of biomarkers in drain fluid is indicative of disease severity and whether a disease is progressing or regressing. For example, if drain fluid is measured at multiple time points, it is possible to calculate a slope of biomarker accumulation. The steepness of the slope is indicative of the velocity of change (either negative or positive). In the same way, the area under the curve resulting from multiple measurements in the drain fluid is indicative of disease progression or regression.

DETAILED DESCRIPTION

The present invention provides methods for disease diagnosis comprising the steps of obtaining drain fluid from an interventional procedure, identifying in the fluid a biomarker indicative of disease, and diagnosing a disease or condition based on the presence of the biomarker in the fluid.

The present invention is based on the discovery that what has conventionally been considered, for example, surgical waste fluid, actually is a rich source of diagnostic content.

Lymphatic Fluid

The lymphatic or lymph system is central to the body's immune system. The system contains lymphatic vessels that collect lymphatic fluid from peripheral tissues of the body and transport it to lymphatic ducts. Lymph nodes of the system contain immune cells to fight infections and filter extra-cellular materials (e.g., cellular debris and byproducts, damaged cells, cancer cells, and pathogens) from the lymph fluid. The right lymphatic duct and thoracic duct drain lymph fluid collected from the lymphatic system and return it to the bloodstream via the subclavian vain.

The lymph system is associated with many types of cancer and other pathologies. For example, cells of the lymph system itself, such as in the lymph nodes, can be the source of cancers, such as lymphomas. Moreover, the lymph system can remove cancer cells (e.g., those the break away from a tumor) or other pathogens from a peripheral tissue of the body as part of its immune system functioning. Occasionally, cancer cells attach to a portion of the immune system, including after collection, and begin to grow. This metastasis is often exacerbated as the lymph system continues to circulate newly grown cancer cells throughout the system, and by extension, the body. Thus, for example, many cancers of the head, neck, breast, and glandular systems are associated with metastasis or other changes in the lymphatic system.

Accordingly, many surgical interventions involve the lymphatic system. This may include direct interventions of the lymphatic system, such as resection, dissection, or excision surgeries to remove a diseased portion of the lymphatic system or to obtain tissue samples. Additionally, given its role in the immune system, many surgical interventions, which do not directly target the lymphatic system, often require collecting and discarding lymphatic fluid, for example, during or after treatments to manage lymph fluid overload or facilitate wound healing. Often, as part of a postoperative regime, patients receive an implanted surgical drain, such as a JP drain, which removes lymph fluid that collects at the site of a surgery.

Biomarkers and Identification

The biomarker identified by the present invention may be any known biomarker for a given disease present in surgical fluid.

For example, the biomarker may comprise tumor cells, immune cells, bacterial cells, viral host cells, donor organ cells, microvascular cells, cell-free DNA, cell-free RNA, circulating tumor DNA, messenger RNA, miRNA, exosomes, proteins, hormones, and other analytes. The biomarker identified may depend on, for example, a specific patient, pathology, surgery type, and surgery site. By analyzing biomarkers in the obtained fluid, methods of the invention may provide diagnostic or prognostic information. For example, by identifying circulating tumor cells or cell-free tumor DNA, cancer may be diagnosed in the subject.

In various aspects, biomarkers may be identified and quantified using methods known in the art. Suitable assays include, for example, nucleic acid sequencing, PCR, quantitative PCR, digital droplet PCR, Western blot target capture, proteomics, nucleic acid expression analysis, and antibody screening. For example, assays may include whole genome sequencing, next generation DNA sequencing, next generation RNA sequencing, multiplex PCR, methylation analysis, droplet PCR, droplet cell separation, or any combination thereof.

Fluorescent labels may be used to identify biomarkers. A fluorescent label or fluorescent probe, is a molecule that is attached chemically to aid in the detection of a biomarker. Fluorescent labeling generally uses a reactive derivative of a fluorescent molecule known as a fluorophore. The fluorophore selectively binds to a specific region or functional group on the biomarker and can be attached chemically or biologically. Any known technique for fluorescent labeling may be used, for example enzymatic labeling, protein labeling, or genetic labeling. Any known fluorophore may also be used. Both the fluorophore and labelling technique may be selected and adjusted based on the biomarker to be identified. The most commonly labelled molecules are antibodies, proteins, amino acids and peptides which are then used as specific probes for detection of a particular target.

Fluorescent labelling may be used to identify and quantify a biomarker in the surgical fluid sample without separating the components of the surgical fluid. For example, by providing fluorescent labels directly into the surgical fluid, fluorescent microscopy or a colorimetric assay can be used to identify and quantify the presence of the biomarker from a color change alone. For example, fluorescent labels may be applied to the surgical fluid in the surgical-suite during the surgical procedure to provide valuable information to the surgeon.

When quantifying a biomarker, barcodes may be added to biomarker to aid in amplification, detection, or differentiation of the biomarker. Barcodes may be added to biomarkers by "tagging" the biomarker with the barcode. Tagging may be performed using any known method for barcode addition, for example direct ligation of barcodes to one or more of the ends of a nucleic acid molecule or protein. Nucleic acid molecules may, for example, be end repaired in order to allow for direct or blunt-ended ligation of the barcodes. Barcodes may also be added to nucleic acid molecules through first or second strand synthesis, for example using capture probes or primers. First and second strand synthesis is advantageously used in RNA analysis to generate tagged DNA molecules.

Unique molecular identifiers are a type of barcode that may be provided to biomarkers in a sample to make each biomarker, together with its barcode, unique, or nearly unique. For example, with regard to nucleic acid molecules, this is accomplished by adding, e.g. by ligation or reverse transcription, one or more UMIs to each nucleic acid molecule such that it is unlikely that any two previously identical nucleic acid molecules, together with their UMIs, have the same sequence. By selecting an appropriate number of UMIs, every nucleic acid molecule in the sample, together with its UMI, will be unique or nearly unique. One strategy for doing so is to provide to a sample of nucleic acid molecules a number of UMIs in excess of the number of starting nucleic acid molecules in the sample. By doing so, each starting nucleic molecule will be provided with different UMIs, therefore making each molecule together with its UMIs unique. However, the number of UMIs provided may be as few as the number of identical nucleic acid molecules in the original sample. For example, where no more than six nucleic acid molecules in a sample are likely to be identical, as few as six different UMIs may be provided, regardless of the number of starting nucleic acid molecules.

UMIs are also advantageous in that they can be useful to correct for errors created during amplification, such as amplification bias or incorrect base pairing during amplification. For example, when using UMIs, because every nucleic acid molecule in a sample together with its UMI or UMIs is unique or nearly unique, after amplification and sequencing, molecules with identical sequences may be considered to refer to the same starting nucleic acid molecule, thereby reducing amplification bias. Methods for error correction using UMIs are described in Karlsson et al., 2016, "Counting Molecules in cell-free DNA and single cells RNA", Karolinska Institutet, Stockholm Sweden, the contests of which are incorporated herein by reference.

For RNA or mRNA sequencing, sequencing may first comprise the step of preparing a cDNA library from barcoded RNA, for example through reverse transcription, and sequencing the cDNA. cDNA sequencing may advantageously allow for the quantification of gene expression within the single cell, and can be useful to identify characteristics of the single cell to, for example, make a diagnosis, prognosis, or determine drug effectiveness.

Reverse transcription may be performed using without limitation dNTPs (mix of the nucleotides dATP, dCTP, dGTP and dTTP), buffer/s, detergent/s, or solvent/s, as required, and suitable enzyme such as polymerase or reverse transcriptase. The polymerase used may be a DNA polymerase, and may be selected from Taq DNA polymerase, Phusion polymerase (as provided by Thermo Fisher Scientific, Waltham, Massachusetts), or Q5 polymerase. Nucleic acid amplification reagents are commercially available, and may be purchased from, for example, New England Biolabs, Ipswich, MA, USA. The reverse transcriptase used in the presently disclosed targeted library preparation method may be for example, maxima reverse transcriptase. In some embodiments, the general parameters of the reverse transcription reaction comprise an incubation of about 15 minutes at 25 degrees and a subsequent incubation of about 90 minutes at 52 degrees.

Reverse transcription may be performed by oligos that have a free, 3' poly-T region. The 3' portions of the cDNA capture oligos may include gene-specific sequences or oligomers, for example capture primers to reverse transcribe RNA guides comprising a capture sequence. The oligomers may be random or "not-so-random" (NSR) oligomers (NSROs), such as random hexamers or NSR hexamers. The oligos may include one or more handles such as primer binding sequences cognate to PCR primers that are used in the amplifying step or the sequences of NGS sequencing adaptors. The reverse transcription primers may include template switching oligos (TSOs), which may include poly-G sequences that hybridize to and capture poly-C segments added during reverse transcription.

Reverse transcription of non-polyadenylated RNA may comprise use of a capture sequence and a capture primer or probe. Primer sequences may comprise a binding site, for example a primer sequence that would be expected to hybridize to a complementary sequence, if present, on any nucleic acid molecule released from a cell and provide an initiation site for a reaction. The primer sequence may also be a "universal" primer sequence, i.e. a sequence that is complementary to nucleotide sequences that are very common for a particular set of nucleic acid fragments. Primer sequences may be P5 and P7 primers as provided by Illumina, Inc., San Diego, California. The primer sequence may also allow a capture probe to bind to a solid support.

Reverse transcription can also be useful for adding a barcode or a UMI, or both to cDNA. This process may comprise hybridizing the reverse transcription primer to the probe followed by a reverse transcription reaction. The complement of a nucleic acid when aligned need not be perfect; stable duplexes may contain mismatched base pairs or unmatched bases. Those skilled in the art of nucleic acid technology can determine duplex stability empirically considering a number of variables including, for example, the length of the oligonucleotide, percent concentration of cytosine and guanine bases in the oligonucleotide, ionic strength, and incidence of mismatched base pairs.

Nucleic acid molecules may advantageously be amplified prior to sequencing. Amplification may comprise methods for creating copies of nucleic acids by using thermal cycling to expose reactants to repeated cycles of heating and cooling, and to permit different temperature-dependent reactions (e.g. by Polymerase chain reaction (PCR). Any suitable PCR method known in the art may be used in connection with the presently described methods. Non limiting examples of PCR reactions include real-time PCR, nested PCR, multiplex PCR, quantitative PCR, or touchdown PCR.

Sequencing nucleic acid molecules may be performed by methods known in the art. For example, see, generally, Quail, et al., 2012, A tale of three next generation sequencing platforms: comparison of Ion Torrent, Pacific Biosciences and Illumina MiSeq sequencers, BMC Genomics 13:341. Nucleic acid molecule sequencing techniques include classic dideoxy sequencing reactions (Sanger method) using labeled terminators or primers and gel separation in slab or capillary, or preferably, next generation sequencing methods. For example, sequencing may be performed according to technologies described in U.S. Pub. 2011/0009278, U.S. Pub. 2007/0114362, U.S. Pub. 2006/0024681, U.S. Pub. 2006/0292611, U.S. Pat. Nos. 7,960,120, 7,835,871, 7,232,656, 7,598,035, 6,306,597, 6,210,891, 6,828,100, 6,833,246, and 6,911,345, each incorporated by reference.

The conventional pipeline for processing sequencing data includes generating FASTQ-format files that contain reads sequenced from a next generation sequencing platform, aligning these reads to an annotated reference genome, and quantifying expression of genes. These steps are routinely performed using known computer algorithms, which a person skilled in the art will recognize can be used for executing steps of the present invention. For example, see Kukurba, Cold Spring Harb Protoc, 2015 (11):951-969, incorporated by reference.

EXAMPLES

Example 1

After neck resection surgery to remove an oropharyngeal tumor, subjects receive an implanted surgical drain, e.g., a JP drain. 24 hours post-surgery, fluid is collected from a lymphatic duct from each subject via the drain. Each fluid sample is centrifuged and filtered. A nuclease, such as EDTA is added to each sample.

Biomarkers associated with oropharyngeal cancer are isolated and measured from the samples, which include tumor-associated genetic material. The tumor-associated genetic material includes, for example, one or more of cell-free nucleic acids, nucleic acids from a tumor, nucleic acids from an isolated exosome, and/or viral nucleic acids.

Once isolated, the tumor-associated genetic material is analyzed using one or more of nucleic acid sequencing, PCR, and/or Western blot.

This analysis of tumor-associated genetic material provides results that may include, for example, quantities of detected nucleic acids, mutations, variants, copy number, and expression patterns. These results may be compared with other bioassay results, either for other biomarkers in the fluid from the lymphatic duct and/or from a different sample type, such as blood or plasma.

Using these results, one or more scores are produced indicative of the subjects' conditions, disease states, and prognosis. The scores provide a practitioner with valuable insight as to whether to pursue additional therapeutic intervention, e.g., additional surgery, medications, and active monitoring.

Incorporation by Reference

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:
1. A method of quantifying gene expression, the method comprising the steps of:
tagging a plurality of RNA with a barcode, the RNA being from a single tumor cell obtained from a drain fluid collected during a surgical procedure;

reverse transcribing the tagged RNA to prepare a barcoded cDNA library; and sequencing the barcoded cDNA library to quantify tumor gene expression.

2. The method of claim 1, wherein the plurality of RNA are tagged by direct ligation of barcodes to one or more ends of the RNA.

3. The method of claim 1, wherein the plurality of RNA are tagged by first or second strand synthesis.

4. The method of claim 3, wherein the first or second strand synthesis uses capture probes or primers.

5. The method of claim 1, wherein the plurality of RNA are tagged with a plurality of barcode.

6. The method of claim 5, wherein each RNA is tagged with a unique molecular identifier (UMI).

7. The method of claim 1, further comprising amplifying the barcoded cDNA library prior to sequencing the barcoded cDNA library.

8. The method of claim 1, wherein the drain fluid is collected using a catheter or a drain port.

9. The method of claim 1, wherein the drain fluid is collected using suction.

10. The method of claim 1, wherein the drain fluid is collected by irrigating a surgical site with water or saline.

11. The method of claim 1, wherein the plurality of RNA comprises messenger RNA (mRNA) or miRNA.

12. The method of claim 11, wherein the plurality of RNA consists of mRNA.

13. The method of claim 1, further comprising repeating the method with RNA from a post-operative sample of lymphatic fluid.

14. The method of claim 1, further comprising separating a lymphatic fluid from the drain fluid, and wherein the single tumor cell is obtained from the separated lymphatic fluid.

* * * * *